US005668227A

United States Patent [19]
Wolleb et al.

[11] Patent Number: 5,668,227
[45] Date of Patent: Sep. 16, 1997

[54] CYCLOHEXYL-GROUP-CONTAINING GLYCIDYL ETHERS

[75] Inventors: Heinz Wolleb, Marly; Andreas Kramer, Düdingen, both of Switzerland

[73] Assignee: Ciba-Geigy Corporation, Tarrytown, N.Y.

[21] Appl. No.: 613,393

[22] Filed: Mar. 11, 1996

Related U.S. Application Data

[63] Continuation of Ser. No. 385,382, Feb. 7, 1995, abandoned, which is a continuation of Ser. No. 147,656, Nov. 4, 1993, abandoned.

[30] Foreign Application Priority Data

Nov. 11, 1992 [CH] Switzerland ............... 3488/92

[51] Int. Cl.$^6$ ............................. C08G 59/20
[52] U.S. Cl. .............. 525/507; 528/407; 528/418; 549/552; 549/560
[58] Field of Search ............. 549/552, 560; 528/407, 418; 525/507

[56] References Cited

U.S. PATENT DOCUMENTS

| | | | |
|---|---|---|---|
| 2,538,072 | 1/1951 | Zech | 549/516 |
| 3,244,731 | 4/1966 | Winfield et al. | 260/348 |
| 3,327,016 | 6/1967 | Lee | 260/830 |
| 3,535,378 | 10/1970 | Cross et al. | 260/563 |
| 4,088,614 | 5/1978 | Mori et al | 260/2.5 |
| 4,767,883 | 8/1988 | Molaire | 560/220 |
| 4,847,394 | 7/1989 | Schuster | 549/540 |
| 5,128,491 | 7/1992 | Cheng | 549/516 |
| 5,304,662 | 4/1994 | Thoseby et al. | 549/560 |

FOREIGN PATENT DOCUMENTS

| | | |
|---|---|---|
| 0467290 | 1/1992 | European Pat. Off. . |
| 0552864 | 7/1993 | European Pat. Off. . |
| 2528022 | 1/1977 | Germany . |
| 4139255 | 6/1993 | Germany . |
| 760744 | 11/1956 | United Kingdom . |
| 1053193 | 12/1966 | United Kingdom . |

OTHER PUBLICATIONS

Translated copy of Japan Kokai Hei 1–151567 Dec. 1987.
Derwent Abstract 05830y/04.
Chemical Abstract 87: 6630y.
Chemical Abstract 93: 71525f for JP–A–79141708.
Chemical Abstract 107: 187292q for JP–A–62136658.
Chemical Abstract 104: 43225K for JP–A–60131289.
Tetrahedron Letters, vol. 29, No. 18, pp. 2215–2218, 1988.
Chemical Abstract 90: 22373j.
Synthesis, Mar. 1978, pp. 223–225.
Chemical Abstracts 112: 21404, "Preparation of Aliphatic Glycidyl Ethers In High Purity", Suzuki et al.
Chemical Abstracts 111: 116273, "Purification of Epoxy Resins", Taira Harada.

*Primary Examiner*—Frederick Krass
*Attorney, Agent, or Firm*—David R. Crichton; William A. Teoli

[57] ABSTRACT

Novel cyclohexyl-group-containing glycidyl ethers of formulae I to IV according to claim 1, which are distinguished especially by a low chlorine content and a low viscosity and which can be used, for example, in epoxy resin formulations as reactive diluents, flexibilisers or adhesion enhancers, or can also be polymerised per se and used as coatings or casting resins, the products having only slight water absorption and having good external weather resistance.

11 Claims, No Drawings

CYCLOHEXYL-GROUP-CONTAINING GLYCIDYL ETHERS

This application is a continuation of application Ser. No. 08/385,382 filed Feb. 7, 1995, now abandoned which is a continuation of application Ser. No. 08/147,656 filed Nov. 4, 1993, now abandoned.

The present invention relates to novel cyclohexyl-group-containing glycidyl ethers, to processes for their preparation and to their use, for example, in epoxy resin formulations as reactive diluents, flexibilisers or adhesion enhancers.

Numerous cyclohexyl-group-containing glycidyl ethers, which are generally referred to as epoxy resins, are known and they can be prepared in accordance with known procedures. Those procedures consist in principle of a catalysed condensation of a suitable cyclohexyl-group-containing hydroxy compound with epichlorohydrin or a derivative thereof in the presence of a Lewis acid. Those procedures are associated inter alia with the disadvantage that in the epoxy resins prepared in that manner there is a high proportion of organically bonded chlorine (more than about 1.0% by weight) which has an adverse effect (for example corrosion, yellowing) in the products of further processing (see, for example, DE-A-2 528 022). On the other hand, it is proposed according to DE-A-3 629 632 selectively to hydrogenate the aromatic ring in glycidyl ethers based on aromatic building blocks, for example bisphenol A, bisphenol F, phenol- and cresol-novolaks.

The aim of the invention is therefore to find a way in which, on the one hand, it is possible to prepare economically cyclohexyl-group-containing glycidyl ethers having a low chlorine content and, on the other hand, in which at the hydrogenation stage aromatic rings are hydrogenated with the simultaneous opening of the oxirane ring.

The solution lies in a process that does not use a Lewis acid. It has been found that alcohols that contain an ether or amino group in the β-position can be reacted satisfactorily with epihalohydrin using a phase transfer process and as a result yield resins having a low chlorine content.

Accordingly the invention relates to a process which is novel for those epoxy resins and to novel epoxy resins.

The novel epoxy resins, which are cyclohexyl-group-containing glycidyl ethers, are compounds corresponding to the following formulae I to IV:

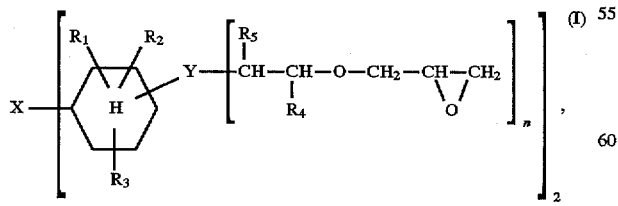

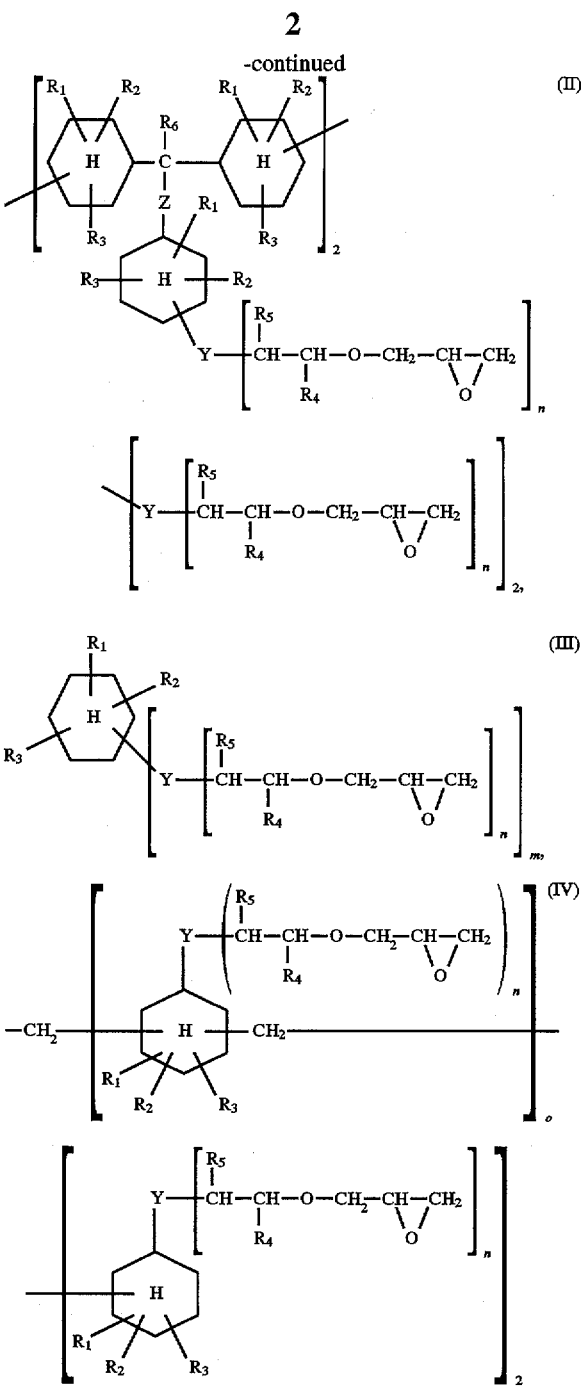

wherein the individual symbols are defined as follows:

$R_1$, $R_2$ and $R_3$ are each independently of the others hydrogen, an unsubstituted or substituted $C_1$–$C_{10}$alkyl radical or a hydrogenated aryl radical;

$R_4$ and $R_5$ are each independently of the other hydrogen or a $C_1$–$C_{20}$alkyl radical;

$R_6$ is hydrogen, an unsubstituted or substituted $C_1$–$C_{10}$alkyl radical or a hydrogenated aryl radical;

X is a bridge member of the formula —CH$_2$—, —C(CH$_3$)$_2$—, —C(CF$_3$)$_2$—, —CO—, —O—, —S—, —SO$_2$—,

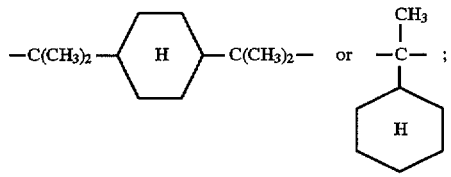

Y=O (when n=1) or N (when n=2);
m is the number 1, 2 or 3;
n=1 (when Y=O) or 2 (when Y=N);
o is a number from 1 to 30; and
Z is a direct bond or a bridge member of the formula —CH$_2$— or

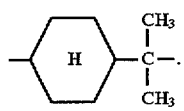

Preferred compounds are symmetrical and X and Y (in formula I) are in the p-position relative to one another, and the three Y (in formula II) are each in the p-position relative to C (carrying R$_6$) or Z, as the case may be.

Also preferred are those compounds of formulae I to IV wherein, independently of one another, R$_1$, R$_2$ and R$_3$ are hydrogen and/or an alkyl radical, especially a CH$_3$ radical;

R$_4$ and R$_5$ are hydrogen and/or CH$_3$;

R$_6$ is hydrogen;

X is a bridge member of the formula 13 CH$_2$—, —C(CH$_3$)$_2$—, —C(CF$_3$)$_2$—, —CO—, —O— or —SO$_2$—;

Y is O;

n is the number 1;

Z is a direct bond or the bridge member —CH$_2$—;

m is the number 2 or 3; and o is a number from 1 to 20 and especially from 1 to 15.

The compounds of formulae I and IV are of particular importance.

When R$_1$, R$_2$, R$_3$ and R$_6$ in the above formulae I to IV are an unsubstituted or substituted C$_1$-C$_{10}$alkyl radical, they may be straight-chain or branched alkyl radicals, such as methyl, ethyl, propyl, isopropyl, butyl, sec-butyl, tert-butyl, pentyl, isopentyl, hexyl, isohexyl and octyl; all those alkyl radicals may be mono- or poly-substituted by, for example, cyclohexyl and/or halogen, such as F, Cl or Br.

When R$_1$, R$_2$, R$_3$ and R$_6$ are a hydrogenated aryl radical, it is especially a hydrogenated benzene or naphthalene radical.

R4 and R$_5$ as a C$_1$-C$_{20}$alkyl radical may be a straight-chain or branched alkyl radical. Examples thereof are methyl, ethyl, propyl, isopropyl, butyl, sec-butyl, pentyl, isopentyl, hexyl, octyl, n-decyl, dodecyl, tetradecyl and octadecyl.

In the preferred compounds of formula I

R$_1$, R$_2$ and R$_3$ are hydrogen and/or a C$_1$-C$_{10}$alkyl radical, especially a CH$_3$ radical.

R$_4$ and R$_5$ are hydrogen and/or CH$_3$,

Y is O, n is 1, and

X is a bridge member of the formula 13 CH$_2$—, —C(CH$_3$)$_2$—, —C(CF$_3$)$_2$—, —CO—, —O— or —SO$_2$—.

In the preferred compounds of formula II

R$_1$, R$_2$ and R$_3$ are hydrogen and/or a C$_1$-C$_{10}$alkyl radical, especially a CH$_3$ radical, R$_4$ and R$_5$ are hydrogen and/or CH$_3$, R$_6$ is hydrogen, Y is O, n is 1, and Z is a direct bond or a bridge member —CH$_2$—.

In the preferred compounds of formula III

R$_l$, R$_2$ and R$_3$ are hydrogen and/or a C$_1$-C$_{10}$alkyl radical, especially a CH$_3$ radical, R$_4$ and R$_5$ are hydrogen and/or CH$_3$, Y is O, n is 1, and m is 2 or 3, and when m is the number 2, the two Y radicals are preferably in the 1,3,-position relative to one another, and when m is 3, the three Y radicals are preferably in the 1,3,5-position.

In the preferred compounds of formula IV

R$_1$, R$_2$ and R$_3$ are hydrogen and/or a C$_1$-C$_{10}$alkyl radical, especially a CH$_3$ radical, R$_4$ and R$_5$ are hydrogen and/or CH$_3$, Y is O, n is 1, and o is a number from 1 to 20, especially from 1 to 15.

All the compounds of formulae I to IV that contain cycloaliphatic and oxirane members are at 20° C. generally colourless to yellow liquids having a viscosity of from 10 to 4000 mPa.s, especially from 100 to 500 mPa.s, and are distinguished especially by a very low chlorine content of less than 0.4% by weight. They can be characterised by means of their epoxy content, chlorine content, molecular weight distribution (Mn, Mw) and their viscosity.

The compounds of formulae I to IV can be prepared, for example, according to two different processes a) and b):

Process a)

In accordance with this process, a compound of formula I, II, III or IV can be prepared as follows:

An aromatic starting compound of formula Ia, IIa, IIIa or IVa, which compounds are known and can be prepared in known manner,

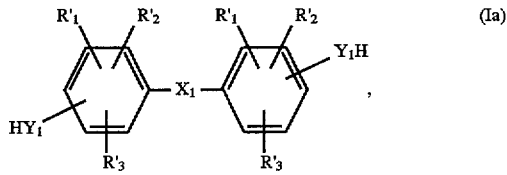
(Ia)

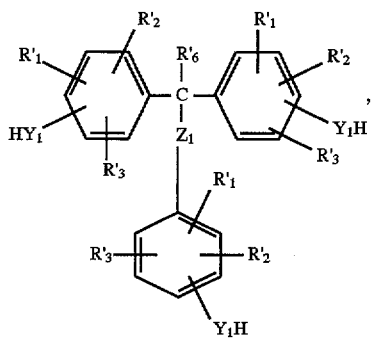

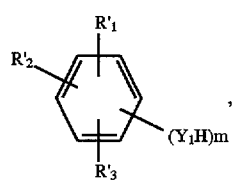

(IIIa)

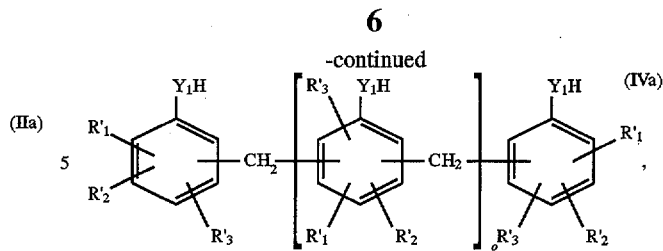

is in a first reaction step reacted in accordance with known processes advantageously with an approximately equimolar amount (±5%) of ethylene oxide or a derivative thereof of the formula

wherein $R_4$ and $R_5$ are as defined under formulae I to IV, in the presence of a base in an organic solvent at a temperature of approximately from 50° to 200° C. and a pressure of from 1 to 10 bar. A compound of formula Ib, IIb, IIIb or IVb so obtained

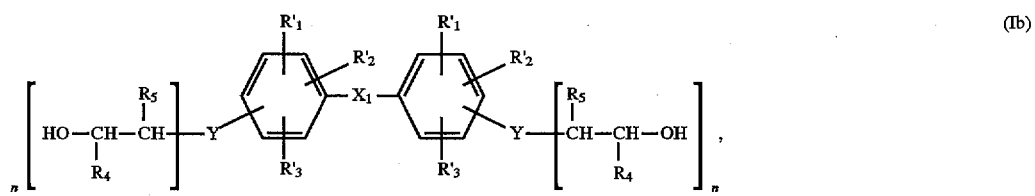

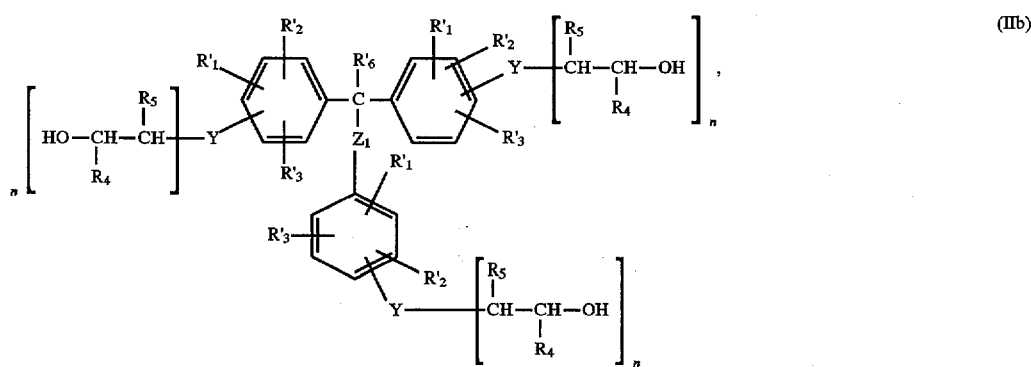

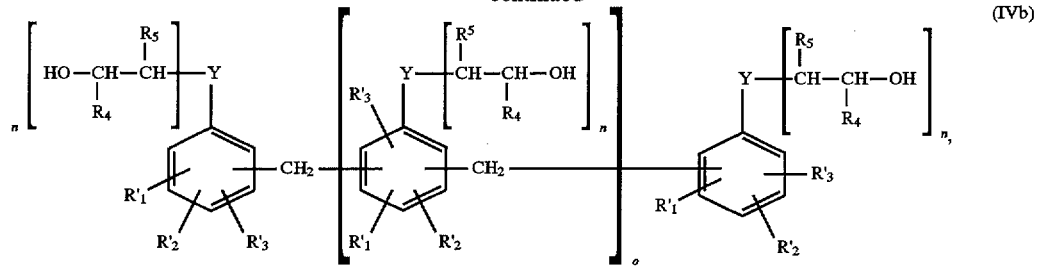

(IVb)

some of which compounds are likewise known, is isolated and in a second reaction step catalytically hydrogenated. The hydrogenation is effected in accordance with known processes by means of hydrogen and a catalyst, advantageously in an organic solvent at a temperature of approximately from 50° to 200° C. and a pressure of from 50 to 200 bar for about 2 to 24 hours.

A hydrogenated compound of formula Ic, IIc, IIIc or IVc so obtained excess epihalohydrin, for example epichlorohydrin, in the presence of a phase transfer catalyst at a temperature of from 40° to 90° C. and a pressure of from 50 to 200 torr with the addition of an alkaline solution, to form a novel compound of formula I, II, III or IV, respectively.

In the above starting materials and intermediates the symbols have the same meanings as the corresponding symbols in the compounds of formulae I to IV according to the invention, with the exception of the aryl radical in $R'_1$,

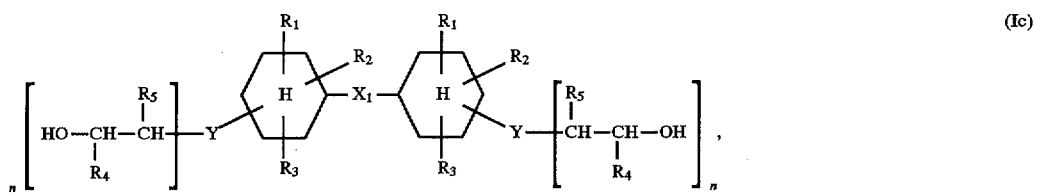

(Ic)

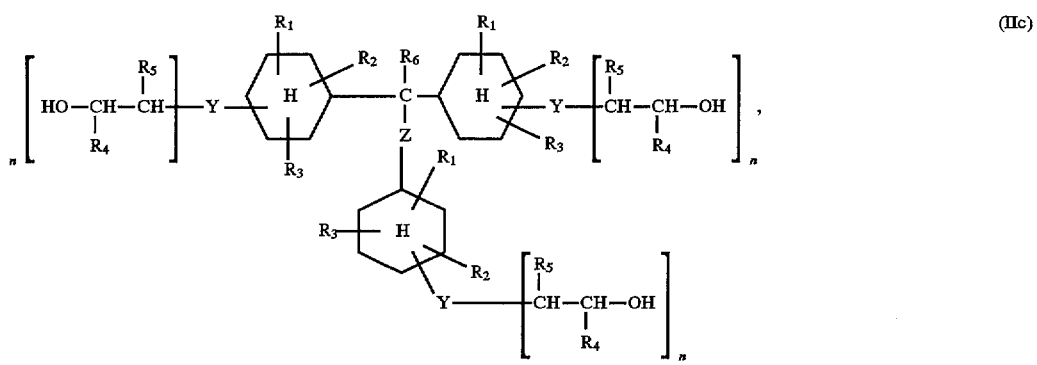

(IIc)

(IIIc)

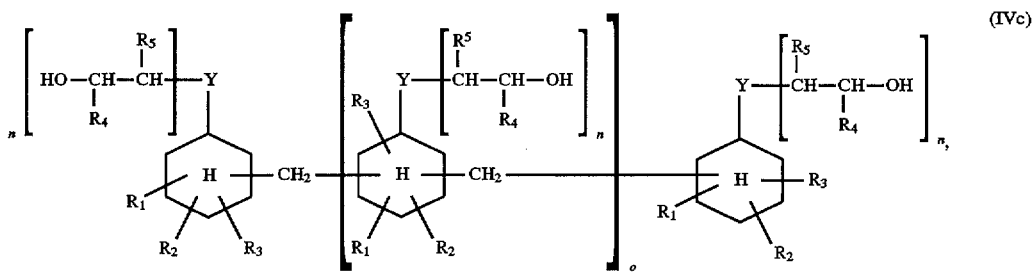

(IVc)

which compounds are novel and to which the present invention likewise relates, is isolated and in a third reaction step reacted in accordance with known processes with $R'_2, R'_3, R'_6, X_1$ and $Z_1$, where the aryl radical is in each case a non-hydrogenated aryl radical, and $Y_1$, which is O or NH.

Process b)

This process provides a method of preparing a compound of formula I, II, III or IV wherein $R_4$ is $CH_3$ and $R_5$ is H.

A starting compound of formula $Ia_1$, $IIa_1$, $IIIa_1$ or $IVa_1$, which compounds are known and can be prepared in known manner,

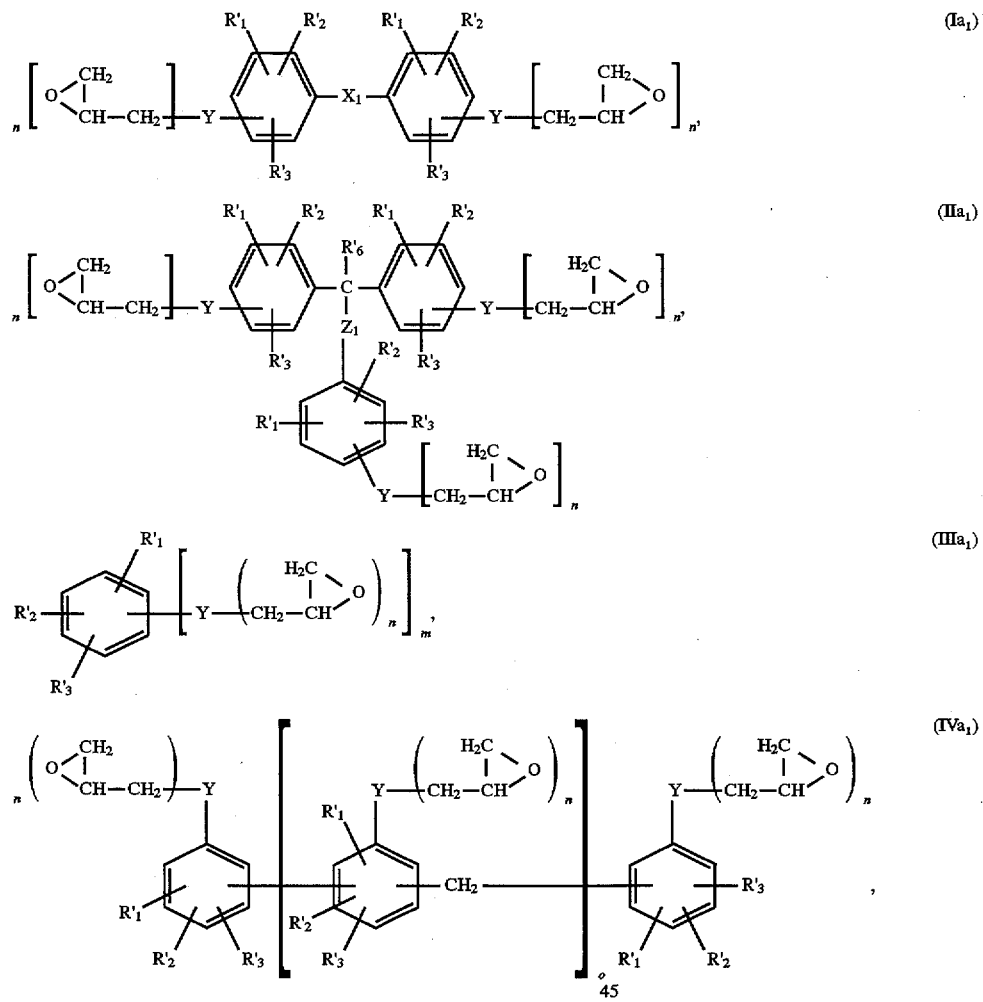

is in a first reaction step catalytically hydrogenated. The hydrogenation is carried out in accordance with known processes by means of hydrogen and a catalyst, advantageously in an organic solvent at a temperature of approximately from 50° to 200° C. and a pressure of from 50 to 200 bar for about 2 to 24 hours. A hydrogenated compound $Ib_1, IIb_1, IIIb_1$ or $IVb_1$ so obtained

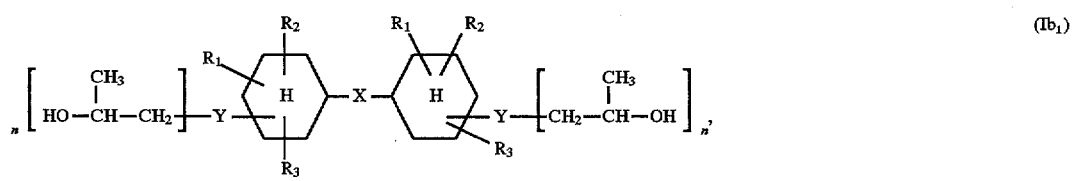

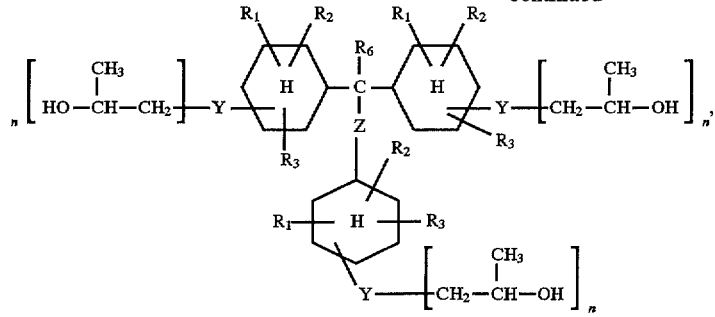 (IIb₁)

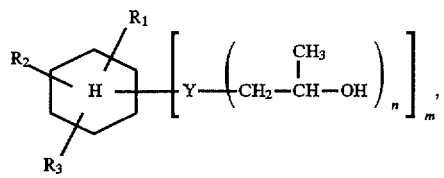 (IIIb₁)

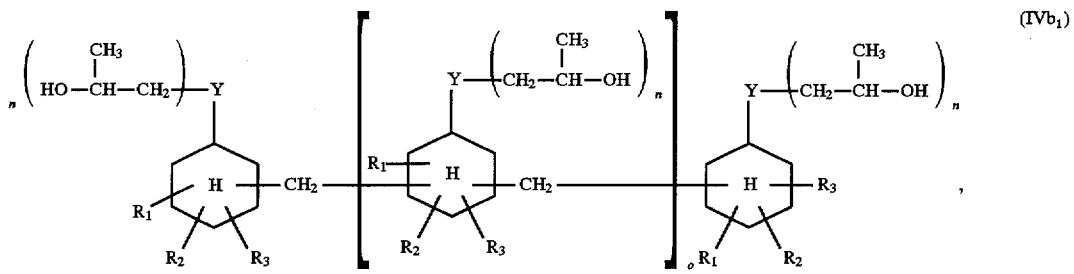 (IVb₁)

which compounds are novel and to which the present invention likewise relates, is isolated and in a second reaction step reacted according to known processes with excess epihalohydrin, for example epichlorohydrin, in the presence of a phase transfer catalyst at a temperature of from 40° to 90° C. and a pressure of from 50 to 200 torr with the addition of an alkaline solution, to form a novel compound of formula I, II, III or IV, respectively, wherein R4 is CH₃ and R₅ is H.

A suitable epihalohydrin is, for example, epibromohydrin and especially epichlorohydrin. The bases used in the first reaction step in Process a) are, for example, secondary and tertiary amines, for example N-ethyl diisopropylamine, triethylamine, tripropylamine, tri-butylamine and triisobutylamine.

Suitable organic solvents are, for example, aromatic hydrocarbons, such as xylene or mesitylene, and especially aliphatic or cycloaliphatic ketones, such as methyl isobutyl ketone, diisobutyl ketone, 2,4-dimethyl-6-heptanone, 2-heptanone, 3-heptanone, cyclopentanone, methylcyclopentanone, cyclohexanone and methylcyclohexanone. The preferred solvent is methyl isobutyl ketone. It is also possible, however, to use mixtures of different solvents. The solvent will advantageously be used in amounts of from 10 to 90% by weight, based on the total reaction mixture.

The reaction temperature is advantageously approximately from 50° to 200° C., preferably approximately from 140° to 160° C. and especially 150° C.

The reaction pressure ranges from 1 to 10 bar and especially from 4 to 6 bar.

The hydrogenation in Processes a) and b) is carded out with hydrogen and a catalyst. Suitable catalysts are, for example: Raney nickel, ruthenium, rhodium, palladium and platinum. Those catalysts can be on inert carrier materials, such as especially active carbon, on sulfates, carbonates or oxides of Mg, Ba, Zn, Al, Fe, Cr and Zr, such as MgO, ZiO₂, TiO₂ and α-Al₂O₃, or on silica gel.

Suitable organic solvents in the hydrogenation reaction step are, for example: alcohols, such as methanol and especially ethanol or methyl Cellosolve, ethers, such as tetrahydrofuran, and esters, such as ethyl acetate.

The hydrogenation is advantageously carried out at a temperature of from 50° to 200° C., especially from 80° to 180° C., at a pressure of from 50 to 200 bar, especially from 100 to 160 bar, and for a period of about 2 to 24 hours, especially from 10 to 15 hours.

The subsequent reaction with epihalohydrin in Processes a) and b) is preferably carried out with an excess of from 2 to 6 mol per OH group of the compound of formula Ic, IIc, IIIc or IVc, or Ib₁, IIb₁, IIIb₁ or IVb₁, respectively.

Suitable phase transfer catalysts are all the compounds known to the person skilled in the art, for example quaternary ammonium salts and phosphonium salts, such as, for example, the tetraalkylammonium hydroxides and halides mentioned in U.S. Pat. No. 4,465,722, and also the piperidinium, morpholinium and pyrrolidinium salts described in U.S. Pat. Nos. 4,885,354, 4,973,648 and 5,006,626, such as, for example: tetramethylammonium chloride, tetrabutylammonium bromide, N,N-dimethylpyrrolidinium chloride, N-ethyl-N-methylpyrrolidinium iodide, N-butyl-N-methylpyrrolidinium bromide, N-benzyl-N-methylpyrrolidinium chloride, N-ethyl-N-methylpyrrolidinium bromide, N-butyl-N-methylmorpholinium bromide, N-butyl-N-methylmorpholinium iodide, N-ethyl-N-hydroxyethylmorpholinium iodide, N-allyl-N-methylmorpholinium bromide, N-methyl-N-benzylpiperidinium chloride, N-methyl-N-benzylpiperidinium bromide, N,N-di-methylpiperidinium iodide, N-methyl-N-ethylpiperidinium acetate or N-methyl-N-ethyl-piperidinium iodide.

Tetramethylammonium chloride is preferably used.

The phase transfer catalysts are used, for example, in an amount of approximately from 0.01 to 10 mol %, preferably from 1 to 5 mol % and especially from 2 to 3 mol %, based on the starting material.

The reaction with the epihalohydrin, for example epichlorohydrin, is advantageously carried out at a temperature of from 40° to 90° C., especially from 50° to 70° C., and a pressure of from 50 to 200 torr, especially from 90 to 110 torr.

To the mixture of the compound of formula Ic, IIc, IIIc or IVc, or Ib$_1$, IIb$_1$, IIIb$_1$ or IVb$_1$, the epihalohydrin and the phase transfer catalyst, which mixture is maintained under reflux, there is preferably added dropwise an aqueous alkali hydroxide solution (alkaline solution), such as a KOH or NaOH solution, especially a 50% aqueous NaOH solution, in the course of from 1 to 5 hours, especially in the course of 2 hours.

The cyclohexyl-group-containing glycidyl ethers of formulae I to IV obtained in accordance with both Process a) and Process b) are then worked up. The working-up is carried out, for example, by cooling the reaction mixture to room temperature, filtering, drying the filtration residue (for example over MgSO$_4$) and removing excess epihalohydrin from the dried product.

There are obtained as residue the cyclohexyl-group-containing glycidyl ethers of formulae I to IV according to the invention in a yield of more than 70% in the form of colourless to yellow liquids or resins (at 20° C.) which have a viscosity of approximately from 10 to 4000 mPa.s, especially from 100 to 500 mPa.s. As a result of the preparation processes those low-viscosity liquids are distinguished especially by a very low chlorine content which in more than 95% of cases is less than 0.4% by weight, especially less than 0.3% by weight.

It is surprising that the novel cyclohexyl-group-containing glycidyl ethers can readily be prepared by the phase transfer process as a result of the fact that the starting materials, β-hydroxy ethers or β-hydroxyamines, contain readily glycidylisable OH groups; furthermore, it is advantageous that it is not necessary to use Lewis acids.

The known starting compounds of formulae Ia to IVa are, for example, dihydroxy or diamino compounds (Ia), compounds having three hydroxy or amino groups (IIa), compounds having one hydroxy group or amino group (IIIa) and compounds having several hydroxy or amino groups (IVa).

Examples of dihydroxy compounds that fall within the scope of formula Ia above are dihydroxyphenols, such as 4,4'-dihydroxydiphenyldimethylmethane (bisphenol A), 4,4'-dihydroxydiphenylmethane, 3,3'-dihydroxydiphenylmethane, 4,4'-dihydroxydiphenyldifluoromethylmethane, 2,2'-dihydroxydiphenyl-ketone, 4,4'-dihydroxydiphenylpropylphenylpropane or 4,4'-dihydroxydiphenylmethylphenylmethane, 4,4'-diaminodiphenylmethane and 4,4'-diaminodiphenyldimethylmethane.

Suitable derivatives of ethylene oxide that can be reacted with those dihydroxy compounds are, for example, in addition to ethylene oxide, propylene oxide and butylene oxide, olefin oxides having a chain length of $C_1$–$C_{20}$; preferably, however, ethylene oxide or propylene oxide is used.

Examples of starting compounds of formula IIa are, for example, 4,4',4"-methylidyne-trisphenol, 4,4',4"-ethylidyne-trisphenol, 4,4'-[1-(4-(1-(4-hydroxyphenyl)-1-methylethyl)-phenyl)ethylidene]-bisphenol and 4,4'-[4-(1-(4-hydroxyphenyl)-1-methyl-ethyl)phenyl)-methylene]-bisphenol.

Examples of starting compounds of formula IIIa are, for example, phenol, aniline, pyrocatechol, resorcinol, phloroglucinol and pyrogallol.

Examples of starting compounds of formula IVa are novolaks and cresol-novolaks.

The compounds of formulae I to IV according to the invention are frequently used in epoxy resin formulations for the modification of certain properties, for example as reactive diluents, flexibilisers or adhesion enhancers. Such formulations optionally comprise additional other epoxy resins, for example bisphenol A epoxy resins or epoxy novolaks, and customary hardening agents, for example amines, carboxylic acid anhydrides, phenols or catalytic hardeners. The formulations are used in an extremely wide variety of applications, for example as surface-coating resins, immersion resins, impregnating resins, adhesives, sealants, sheathing compounds and insulating materials.

As a result of their aliphatic structure the glycidyl ethers according to the invention have excellent external weather resistance.

The compounds according to the invention can also be polymerised per se and used as coatings or as casting resins.

The compounds according to the invention allow the production, for example, of products having low water absorption and good external weather resistance in addition to good general properties.

The following Examples illustrate but do not limit the invention. Rh/C, Pd/C and Ru/C indicate rhodium on carbon, palladium on carbon and ruthenium on carbon, respectively. The abbreviation TMAC represents tetramethylammonium chloride, and MIBK represents methyl isobutyl ketone.

EXAMPLE 1

In an autoclave 320 g (1.01 mol) of 2,2'-bis[4-(2-hydroxyethoxy)phenyl]-propane (prepared, for example, in accordance with JP-A 50105638) are hydrogenated for 11 hours in 2200 ml of ethanol in the presence of 40 g of Rb/C 5% at 80° C. and 160 bar. The reaction mixture is filtered and concentrated by evaporation at 70° C., yielding 316 g (95% of theory) of a slightly yellow oil which according to NMR no longer contains any aromatic compound.

304 g (0.92 mol) of that intermediate are dissolved in 593 ml (7.56 mol) of epichlorohydrin, and 5.5 g of a 50% aqueous solution of TMAC are added. 163.5 g (2.04 mol) of a 50% aqueous NaOH solution are then added dropwise in the course of 2 hours under reflux at an internal temperature of 50°–60° C. and 90 torr, with water simultaneously being removed by azeotropic distillation. The mixture is then allowed to react for a further 2 hours, cooled and filtered, and the resulting product is dried over MgSO$_4$, and the solvent is evaporated off, yielding 398 g (98% of theory) of a slightly yellow resin of the formula below having the following properties:

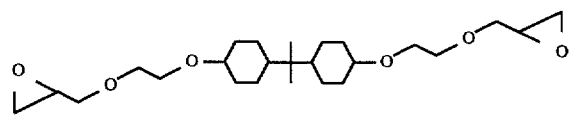

epoxy content: 4.06 eq./kg (89% of theory)
viscosity (25° C.): 240 mPa.s total chlorine content: 0.21% hydrolysable chlorine content: 283 ppm

EXAMPLE 2

139.2 g (3.16 mol) of ethylene oxide are added to 400 g of bisphenol F having an OH content of 7.88 eq./kg, 2.6 g (0.02 mol) of N-ethyl diisopropylamine and 200 ml of MIBK in a suitable autoclave. The reaction mixture is then maintained at 150° C. for 5 hours, the pressure rising to 5.4 bar. The mixture is then cooled, and the solvent is evaporated off in a rotary evaporator, yielding 540 g (100% of theory) of a brown, very viscous oil with the following elemental analysis: C=71.33%, H=6.96%.

536 g of that intermediate are hydrogenated for 14 hours in 2800 ml of ethanol in the presence of 50 g of Rh/C 5% at 95° C. and 160 bar. The reaction mixture is filtered and concentrated by evaporation at 70° C., yielding 547 g of a yellow, viscous oil which according to NMR no longer contains any aromatic compound.

150 g of that intermediate are dissolved in 321 ml (4.1 mol) of epichlorohydrin, and 3.0 g of a 50% aqueous TMAC solution are added. 88.0 g (1.10 mol) of a 50% aqueous NaOH solution are then added dropwise in the course of 1 hour under reflux at an internal temperature of 50°–60° C. and 90 torr, with water simultaneously being removed by azeotropic distillation. The mixture is then allowed to react for a further 1.5 hours, cooled and filtered, and the resulting product is dried over MgSO$_4$, and the solvent is evaporated off, yielding 200 g of a yellow resin of the formula below having the following properties:

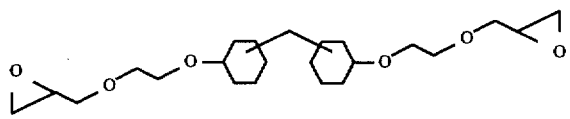

epoxy content: 4.05 eq./kg (84% of theory)

viscosity (25° C.): 360 mPa.s total chlorine content: 0.36% hydrolysable chlorine content: 820 ppm

EXAMPLE 3

58.7 g (1.33 mol) of ethylene oxide are added to 200 g of hardener HT9490 (Ciba-Geigy AG; phenol-novolak) having an OH content of 6.77 eq./kg, 1.7 g (0.013 mol) of N-ethyl diisopropylamine and 200 ml of MIBK in a suitable autoclave. The reaction mixture is then maintained at 150° C. for 5 hours, the pressure rising to 4.0 bar. The mixture is then cooled, and the solvent is evaporated off in a rotary evaporator, yielding 230 g (81% of theory) of an orange solid.

229 g of that intermediate are hydrogenated for 12 hours in 2300 ml of ethanol in the presence of 22 g of Rh/C 5% at 160° C. and 115 bar. The reaction mixture is filtered and concentrated by evaporation at 70° C., yielding 224 g of a yellow solid which according to NMR no longer contains any aromatic compound.

220 g of that intermediate are dissolved in 532 g (5.74 mol) of epichlorohydrin, and 8.4 g of a 50% aqueous TMAC solution are added. 88.0 g (1.10 mol) of a 50% aqueous NaOH solution are then added dropwise in the course of 1 hour under reflux at an internal temperature of 50°–60° C. and 90 torr, with water simultaneously being removed by azeotropic distillation. The mixture is subsequently allowed to react for a further 1.0 hour, then cooled, filtered and dried over MgSO$_4$, and the solvent is evaporated off, yielding 271 g of a yellow resin of the formula below having the following properties:

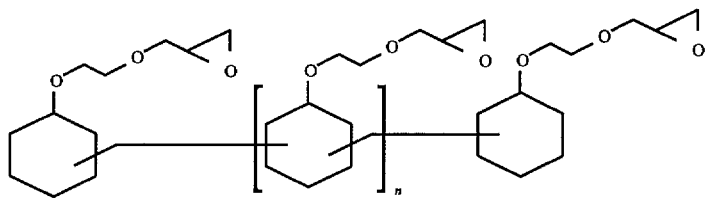

epoxy content: 4.28 eq./kg (90% of theory)

viscosity (25° C.): 3200 mPa.s total chlorine content: 0.20% hydrolysable chlorine content: 380 ppm

EXAMPLE 4

450 g (1.32 mol) of Araldite MY 790 (Ciba-Geigy AG; diglycidyl ether of bisphenol A) are hydrogenated in 4300 ml of methyl Cellosolve in the presence of 22 g of Ru/C 10% at 100 bar and 180° C. The reaction mixture is then cooled and filtered, and the solvent is distilled off in a rotary evaporator. The residue is dissolved in 1 litre of ethyl acetate, washed three times with 100 ml of water, dried over MgSO$_4$, filtered and concentrated by evaporation in a rotary evaporator, yielding 470 g (100% of theory) of a colourless oil which according to NMR no longer contains any aromatic compound and in which epoxy groups can no longer be detected by titration.

285.2 g (0.8 mol) of that intermediate are dissolved in 376 ml (4.75 mol) of epichlorohydrin, and 4.64 g of a 50% aqueous TMAC solution are added. 140.8 g (1.75 mol) of a 50% aqueous NaOH solution are then added dropwise in the course of 2 hours under reflux at an internal temperature of 60°–70° C. and 110 torr with water simultaneously being removed by azeotropic distillation. The mixture is then allowed to react for a further 3.5 hours, cooled, filtered and dried over MgSO$_4$, and the solvent is evaporated off, yielding 325 g (87% of theory) of a yellow resin of the formula below having the following properties:

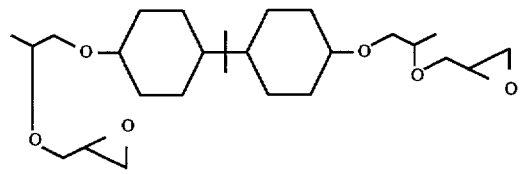

epoxy content: 3.29 eq./kg (77% of theory)

viscosity (25° C.): 440 mPa.s total chlorine content: 0.24% hydrolysable chlorine content: 198 ppm for a further 2 hours, cooled, filtered and dried over MgSO$_4$, and the solvent is evaporated off, yielding 236 g of a yellow resin of the formula below having the following properties:

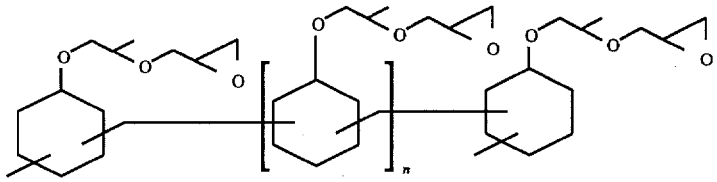

EXAMPLE 5

213 g of Araldite PY 307 (Ciba-Geigy AG; diglycidyl ether of bisphenol F) are hydrogenated in 2130 ml of methyl Cellosolve in the presence of 20 g of Ru/C 10% at 110 bar and 180° C. The reaction mixture is then cooled and filtered, and the solvent is distilled off in a rotary evaporator, yielding 225 g of a slightly yellow oil which according to NMR no longer contains any aromatic compound and in which epoxy groups can no longer be detected by titration.

224 g of that intermediate are dissolved in 520 g (5.60 mol) of epichlorohydrin, and 4.10 g of a 50% aqueous TMAC solution are added. 120.0 g (1.50 mol) of a 50% aqueous NaOH solution are then added dropwise in the course of 1 hour under reflux at an internal temperature of 50°–60° C. and 90 torr, with water simultaneously being removed by azeotropic distillation. The mixture is then allowed to react for a further 2 hours, cooled, filtered and dried over MgSO$_4$, and the solvent is evaporated off, yielding 297 g of a yellow resin having the following properties:

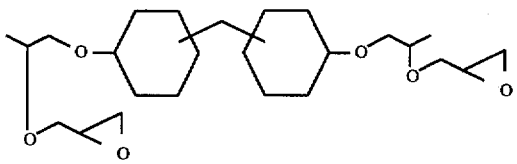

epoxy content: 3.35 eq./kg (74% of theory)

viscosity (25° C.): 320 mPa.s total chlorine content: 0.34% hydrolysable chlorine content: 830 ppm

EXAMPLE 6

267 g of Araldite EPN 1139 (Ciba-Geigy AG; epoxy cresol-novolak) are hydrogenated in 2700 ml of methyl Cellosolve in the presence of 26 g of Pd/C 5% at 115 bar and 160° C. until no more hydrogen is absorbed (30 hours). The reaction mixture is then cooled and filtered, and the solvent is distilled off in a rotary evaporator, yielding 297 g of a slightly yellow oil which according to NMR no longer contains any aromatic compound and in which epoxy groups can no longer be detected by titration.

250 g of that intermediate am dissolved in 560 g (6 mol of epichlorohydrin, and 4.4 g of a 50% aqueous TMAC solution are added. 120.0 g (1.50 mol) of a 50% aqueous NaOH solution are then added dropwise in the course of 1 hour under reflux at an internal temperature of 50°–60° C. and 90 torr, with water simultaneously being removed by azeotropic distillation. The mixture is then allowed to react epoxy content: 3.41 eq./kg (76% of theory)

viscosity (25° C.): 254 mPa.s total chlorine content: 0.66% hydrolysable chlorine content: 240 ppm $M_n$: 503

$M_w$: 796

$M_w/M_n$: 1.58

EXAMPLE 7

15 g of Araldite MY 0510 (Ciba-Geigy AG; 4-aminophenyl triglycide) are hydrogenated in 150 ml of methyl Cellosolve in the presence of 1.5 g of Ru/C at 110° C. and 100 bar until no more hydrogen is absorbed (20 hours). The reaction mixture is then cooled and filtered, and the solvent is distilled off in a rotary evaporator, yielding 15 g of a brown oil which according to NMR no longer contains any aromatic compound and in which only 30% of the theoretical epoxy content remain. 15 g of that intermediate are dissolved in 58 g (0.62 mol) of epichlorohydrin, and 0.46 g of a 50% aqueous TMAC solution are added. 12.8 g (0.16 mol) of a 50% aqueous NaOH solution are then added dropwise in the course of 1 hour under reflux at an internal temperature of 50°–60° C. and 90 torr, with water simultaneously being removed by azeotropic distillation. The mixture is then allowed to react for a further 1 hour, cooled, filtered and dried over MgSO$_4$, and the solvent is evaporated off, yielding 15.32 g of a yellow resin of the formula below having the following properties:

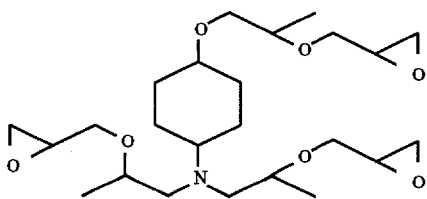

epoxy content: 6.39 eq./kg (97% of theory)

viscosity (25° C.): 150 mPa.s total chlorine content: 0.31% hydrolysable chlorine content: 780 ppm

EXAMPLE 8

121.8 g of the hardener HT 907 (Ciba-Geigy AG; hexahydrophthalic acid anhydride) and 0.7 g of the accelerator DY062 (Ciba-Geigy AG; benzyldimethylamine) are melted at 60° C. and mixed together with stirring. Then 112.0 g of LMB5132 (Ciba-Geigy AG; hexahydrophthalic acid diglycidyl ester) and 28.0 g of the yellow resin prepared according to Example 5 am added and the mixture is homogenised at 60° C. 393.4 g of quartz powder (Quarzwerke Frechen), finely powdered, are sprinkled in, in portions, and mixed in for 10 minutes with stirring at 80° C. The whole mixture is then maintained in vacuo (1 mbar) and with stirring (about 7 min.) until the mixture is free of air. That mixture is then poured into plates preheated to 100° C. and cured for 2 hours at 100° C. and for 16 hours at 140° C.

Plates having the following properties are obtained:

flexural strength: 149 N/mm$^2$ flexural elongation: 1.79 N/mm$^2$ tensile strength (23° C.): 91 N/mm$^2$ double torsion G-$_{IC}$: 486 J/m$^2$ double torsion K-$_{IC}$: 2.3 MPa.m$^{1/2}$ Tg (DSC): 99° C.

EXAMPLE 9

100 g of the resin mixture comprising 60 g of MY-721 (Ciba-Geigy AG: 4,4'-diaminodiphenylmethane-tetraglycide) and 40 g of the yellow resin prepared according to Example 5 are heated to 140° C. 37 g of the hardener HT 976 (Ciba-Geigy AG; 4,4'-diaminodiphenylsulfone) are then added, with stirring. When the hardener has completely dissolved, the mixture is degassed for 5 min. at 10 mm Hg. The mixture is then poured into aluminium moulds (4 mm) of a temperature of 180° C. and hardened for 4 hours at 180° C.

Plates having the following properties are obtained:

Tg$_o$ (TMA): 224° C.

Tg (TMA): 215° C.

modulus of elasticity: 4060±65 MPa strength: 109±22 MPa elongation: 2.7±0.6%

The formulation can be used as a matrix resin together with fibres (carbon, glass, aramide, polyester etc.) to form high quality fibrous composites having a high degree of flexibility and heat stability.

What is claimed is:

1. A cyclohexyl-group-containing glycidyl ether of formula I, II, III or IV having a chlorine content of less than 0.4% by weight and which is prepared from polyhydroxy compounds and epihalohydrin by adding an aqueous alkali hydroxide solution in the presence of a transfer catalyst selected from the group consisting of tetramethylammonium chloride, tetrabutylammonium bromide, N,N-dimethylpyrrolidinium chloride, N-ethyl-N-methylpyrrolidinium iodide, N-butyl-N-methylpyrrolidinium bromide, N-benzyl-N-methylpyrrolidinium chloride, N-ethyl-N-methylpyrrolidinium bromide, N-butyl-N-methylmorpholinium bromide, N-butyl-N-methylmorpholinium iodide, N-ethyl-N-hydroxyethylmorpholinium iodide, N-allyl-N-methylmorpholinium bromide, N-methyl-N-benzylpiperidinium chloride, N-methyl-N-benzylpiperidinium bromide, N,N-dimethylpiperidinium iodide, N-methyl-N-ethylpiperidinium acetate and N-methyl-N-ethylpiperidinium iodide:

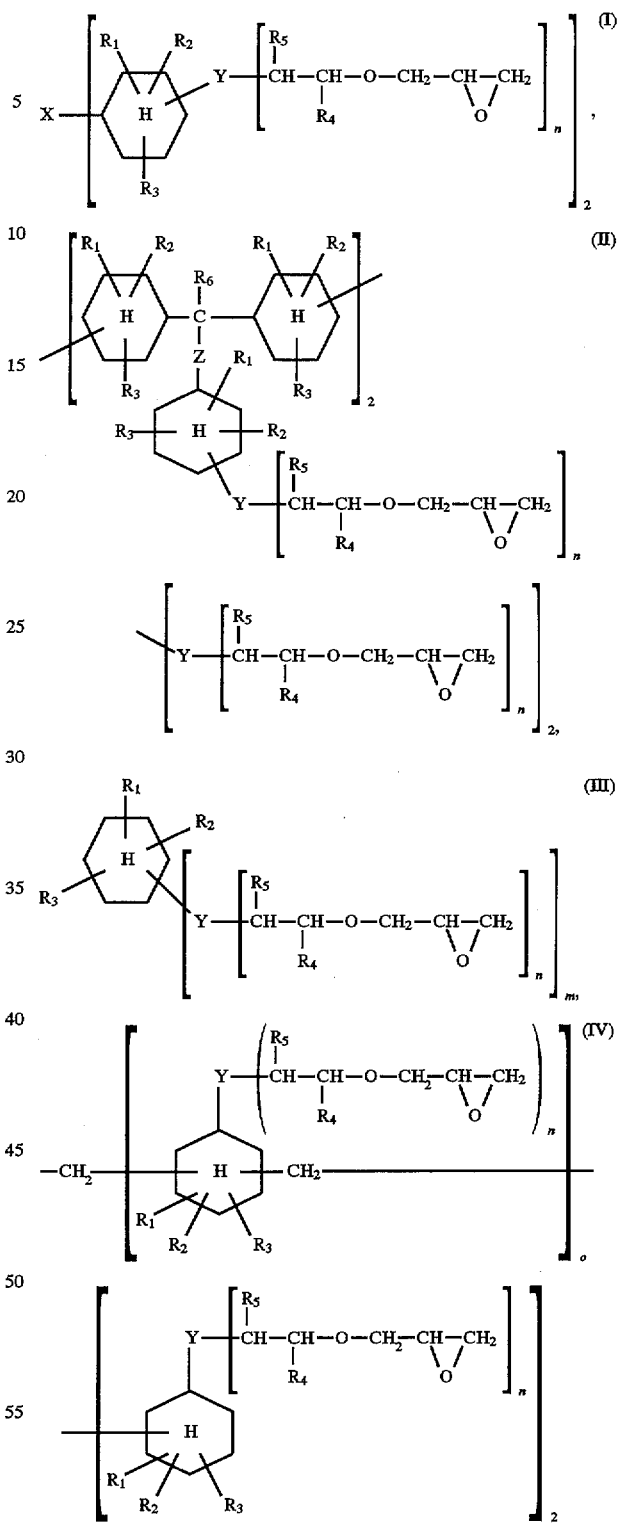

wherein the individual symbols are defined as follows:

$R_1$, $R_2$ and $R_3$ are each independently of the others hydrogen, a $C_1$–$C_{10}$alkyl radical or a hydrogenated aryl radical;

$R_4$ and $R_5$ are each independently of the other hydrogen or a $C_1$–$C_{20}$alkyl radical;

$R_6$ is hydrogen, a $C_1$–$C_{10}$alkyl radical or a hydrogenated aryl radical;

X is a bridge member of the formula —$CH_2$—, —$C(CH_3)_2$—, —$C(CF_3)_2$—, —CO—, —O—, —S—, —$SO_2$—,

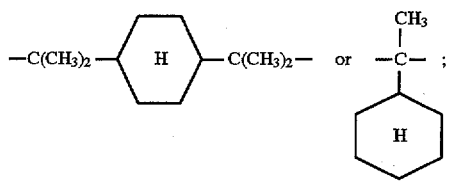

Y=O (when n=1) or N (when n=2);
m is the number 1, 2 or 3;
n=1 (when Y=O) or 2 (when Y=N);
o is a number from 1 to 30; and
Z is a direct bond or a bridge member of the formula —$CH_2$— or

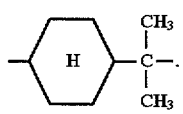

2. A cyclohexyl-group-containing glycidyl ether compound of any one of formulae I to IV according claim 1, wherein the compound is symmetrical and X and Y in formula I are in the p-position relative to C or Z.

3. A cyclohexyl-group-containing glycidyl ether of any one of formulae, I to IV according to claim 1, wherein
$R_1$, $R_2$ and $R_3$ are hydrogen and/or an alkyl radical;
$R_4$ and $R_5$ are hydrogen and/or $CH_3$;
$R_6$ is hydrogen;
X is a bridge member of the formula —$CH_2$—, —$C(CH_3)_2$—, —$C(CF_3)_2$—, —CO—, —O— or —$SO_2$—;
Y is O;
n is the number 1;
Z is a direct bond or the bridge member —$CH_2$—;
m is the number 2 or 3; and
o is a number from 1 to 20.

4. A cyclohexyl-group-containing glycidyl ether of formula I according to claim 1, wherein
$R_1$, $R_2$ and $R_3$ are hydrogen and/or a $C_1$–$C_{10}$alkyl radical;
$R_4$ and $R_5$ are hydrogen and/or $CH_3$,
Y is O,
n is 1, and
X is a bridge member of the formula —$CH_2$—, —$C(CH_3)_2$—, —$C(CF_3)_2$—, —CO—, —O— or —$SO_2$—.

5. A cyclohexyl-group-containing glycidyl ether of formula II according to claim 1, wherein
$R_1$, $R_2$ and $R_3$ are hydrogen and/or a $C_1$–$C_{10}$alkyl radical,
$R_4$ and $R_5$ are hydrogen and/or $CH_3$,
$R_6$ is hydrogen,
Y is O,
n is 1, and
Z is a direct bond or a bridge member —$CH_2$—.

6. A cyclohexyl-group-containing glycidyl ether of formula III according to claim 1, wherein
$R_1$, $R_2$ and $R_3$ are hydrogen and/or a $C_1$–$C_{10}$alkyl radical,
$R_4$ and $R_5$ are hydrogen and/or $CH_3$,
Y is O,
n is 1, and
m is 2 or 3.

7. A cyclohexyl-group-containing glycidyl ether of formula IV according to claim 1, wherein
$R_1$, $R_2$ and R3 are hydrogen and/or a $C_1$–$C_{10}$alkyl radical,
$R_4$ and $R_5$ are hydrogen and/or $CH_3$,
Y is O,
n is 1, and
o is a number from 1 to 20.

8. A method for enhancing the properties of an epoxy resin formulation which comprises adding thereto a property enhancing amount of a cyclohexyl-group containing glycidyl ether of any one of formulae I to IV according to claim 1.

9. A method according to claim 8 wherein said cyclohexyl-group containing glycidyl ether of any one of formulae I to IV functions as a reactive diluent.

10. A method according to claim 8 wherein said cyclohexyl-group containing glycidyl ether of any one of formulae I to IV functions as a flexibiliser.

11. A method according to claim 8 wherein said cyclohexyl-group containing glycidyl ether of any one of formulae I to IV functions as an adhesion enhancer.

* * * * *